United States Patent [19]

Sisti et al.

[11] 4,347,215

[45] Aug. 31, 1982

[54] DEVICE FOR THE AUTOMATION OF AT LEAST ONE OPERATION IN AN INJECTOR FOR GAS CHROMATOGRAPHIC COLUMNS

[75] Inventors: Giorgio Sisti, Melzo; Bruno Tosi, Carate Brianza, both of Italy; Sorin Trestianu, Brussels, Belgium

[73] Assignee: Carlo Erba Strumentazione S.p.A., Italy

[21] Appl. No.: 222,047

[22] Filed: Jan. 2, 1981

[30] Foreign Application Priority Data

Jan. 25, 1980 [IT] Italy ................ 19456 A/80

[51] Int. Cl.³ .................. G01N 1/14; G01N 31/08
[52] U.S. Cl. ................... 422/63; 23/232 C; 73/864.87; 422/89; 422/100
[58] Field of Search ............ 422/100, 63, 65, 89; 23/232 C; 73/864.85, 864.87

[56] References Cited

U.S. PATENT DOCUMENTS

| | | |
|---|---|---|
| 3,096,653 | 7/1963 | Martin et al. |
| 3,174,344 | 3/1965 | Haruki |
| 3,205,711 | 9/1965 | Harris ............... 422/89 X |
| 3,482,451 | 12/1969 | Hrdina |
| 3,508,442 | 4/1970 | Lightner et al. ............. 73/864.87 X |
| 3,529,475 | 9/1970 | Lightner et al. ............. 73/864.87 X |
| 3,550,453 | 12/1970 | Lightner et al. ............. 73/864.87 X |
| 3,566,697 | 3/1971 | Vannus .............. 73/864.87 |
| 3,604,269 | 9/1971 | Smith .............. 73/864.87 |

FOREIGN PATENT DOCUMENTS 1330679 5/1963 France.
1464867 11/1966 France.

Primary Examiner—Ronald E. Serwin
Attorney, Agent, or Firm—Lerner, David, Littenberg & Samuel

[57] ABSTRACT

A device is disclosed for coordinating the position of an injection syringe needle in a gas chromatographic apparatus with at least one other operation of the gas chromatographic apparatus downstream of the device. The device comprises a first channel for introducing the injection syringe. The first channel is substantially aligned with the injection channel of a gas chromatographic injector. The device also includes a position sensor and a lever rotatable around a lever axis substantially perpendicular to the axis of the first channel, wherein the lever has an arm and a shaped appendix, wherein the shaped appendix protrudes into the first channel when the lever is in its rest position, and wherein the appendix is positioned so that, when an injection syringe is introduced into the channel past said point, the injection syringe contacts said appendix and causes rotation of the lever about the lever axis from its rest position so that the arm acts on the position sensor to indicate detection of the presence of the injection syringe in the first channel at said point. The device further includes at least one servomechanism actuatable in response to the detection of the syringe in the channel for controlling the other operation depending on whether or not the injection syringe is detected in the channel.

9 Claims, 6 Drawing Figures

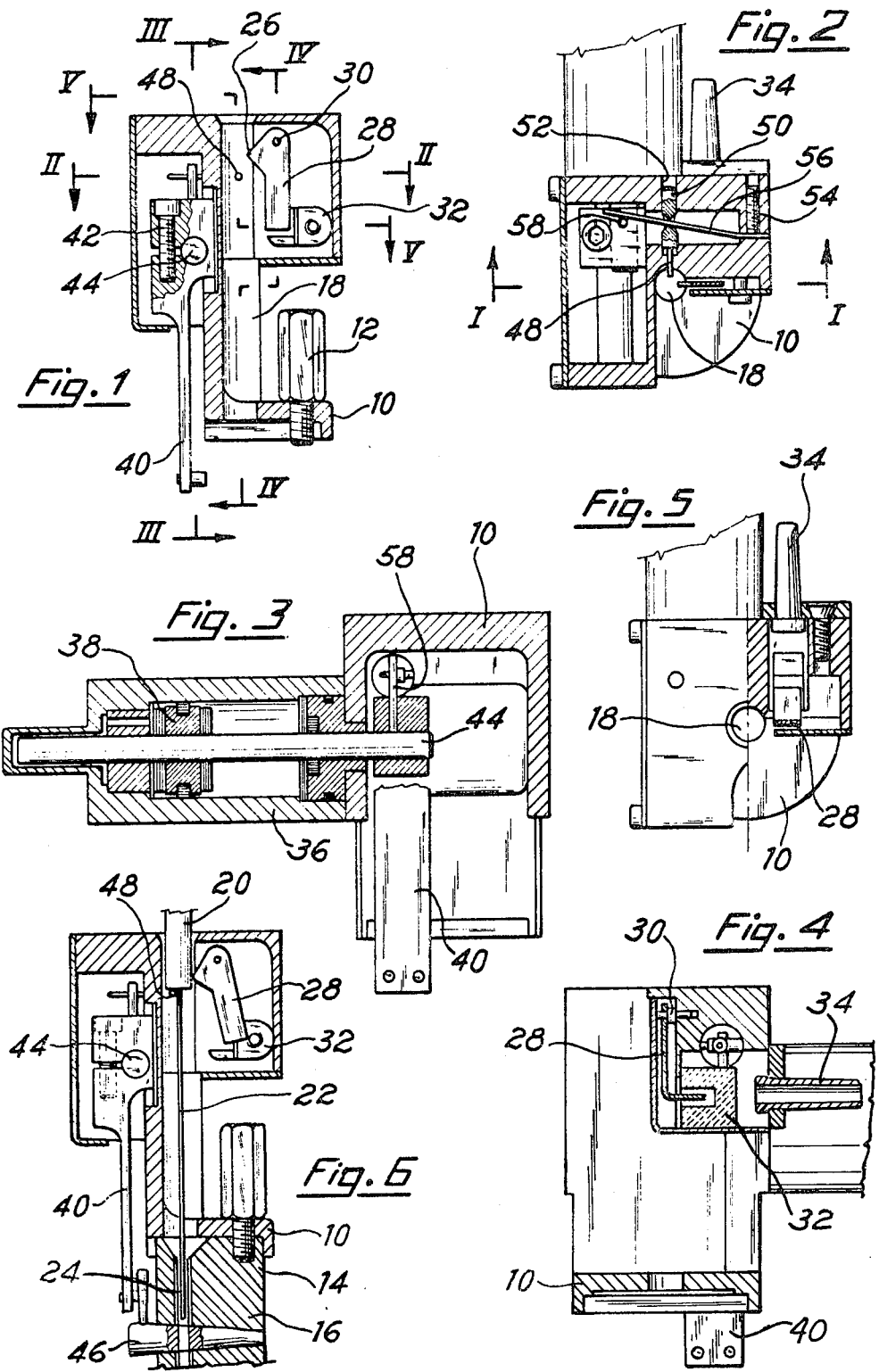

DEVICE FOR THE AUTOMATION OF AT LEAST ONE OPERATION IN AN INJECTOR FOR GAS CHROMATOGRAPHIC COLUMNS

BACKGROUND OF THE INVENTION

1. Field of the Invention

This invention relates to a device, particularly designed to be applied as an accessory to injectors for gas chromatographic columns where the substances to be analysed are introduced by means of an injection syringe, said device being capable of automating at least one of the operations of the injector and/or analytical means downstream the same, due to introduction or drawing back of the syringe.

2. Description of the Prior Art

As it is known, the use of injectors for gas chromatographic columns involves the carrying out, according to the structure and the conditions of injection, of certain operations at the moment of injection and at the end of same. Examples of said operations are opening and closing the injection valve placed inside the channel of some types of injectors; actuating or switching off a secondary cooling device which is used in some types of injectors; opening and closing an exhaust channel, which is open at the end of injection in some types of vaporization injectors; opening or closing an eventual subsidiary injection of carrier gas as performed in correspondence of the valve during injection; and finally switching from feeding conditions at constant pressure to feeding conditions at constant flow of carrier gas. The device can also be coupled with automatic injectors and can even possibly control the flow rate of a sample portion splitting, as well as other functions both of the injector and of analytical means placed downstream the injector itself.

The above mentioned operations are generally performed by the operator who carries out injection of the substance by means of a normal syringe, equipped with a needle which is introduced into the injection channel of injector. However, there is the need to perform these operations with the most possible simultaneousness in relation to the injection syringe introduction or in relation to the drawing back of same. This involves some difficulties for the operator who is already engaged in the delicate operation of sample injection.

SUMMARY OF THE INVENTION

Therefore, an object of this invention is to provide a device to be applied to injectors in order to automate at least one of the operations of the injector and/or analytical means downstream the same, on introduction or drawing back of the syringe by which the operator injects the sample.

Essentially, according to the invention, this device comprises a passage for the injection syringe body, aligned with the injection channel of the injector; at least one detector for detecting the presence of the syringe body in at least one point of said passage; and at least one servomechanism controlled by said detector and actuating on its turn one or more switching valves of the functions the injector and/or analytical means downstream the same. In this way, by means of said detector for the presence of the syringe body and the mechanism controlled by it, it is possible to automatically switch one or more valves controlling the operation of injector and in general of the gas chromatographic analysis unit, with commutation at the moment of syringe introduction or drawing back. The device can also have a safety lock which prevents injection in case the detector-servomechanism combination does not regularly work.

BRIEF DESCRIPTION OF THE DRAWINGS

FIG. 1 is a cross section along a plane passing through the axis of the syringe introduction passage, and showing a device according to the invention, designed for actuating a valve to open and close the injection channel of injector.

FIG. 2 is a partial cross section of the same device along the plane II—II of FIG. 1, said FIG. 2 showing the trace of cutting plane of FIG. 1.

FIG. 3 is a cross section along the plane III—III of FIG. 1.

FIG. 4 is a cross section along the planes indicated by the broken line IV—IV of FIG. 1.

FIG. 5 is a cross section along the planes indicated by the broken line V—V of FIG. 1.

FIG. 6 is a view corresponding to that of FIG. 1 and showing the device applied in working condition to an injector for a gas chromatographic column.

DESCRIPTION OF THE PREFERRED EMBODIMENT

With reference to the drawing, the shown device comprises a support 10 which can be applied to the body of an injector for gas chromatographic columns, for instance by means of a fastening bolt 12 which fits in a threaded opening 14 of the injector body 16 (FIG. 6). The support or frame 10 defines inside itself a passage 18 inside which the body 20 of an injection syringe for samples can be inserted, said syringe showing in a known manner a needle 22 capable of penetrating the injection channel 24 of injector 16.

In at least one point of passage 18 protrudes an appendix 26 of an oscillating lever 28 which is pivoted in 30 on an axis perpendicular to the passage 18 axis. Said lever 28 can freely oscillate and consequently actuate a detector 32 formed by an optical sensor feeded by means of a cable (not shown) passing through a fitting 34.

Said optical detector 32 is capable of actuating a servomechanism formed by a cylinder-piston group, having a cylinder 36 assembled on the body 10 of device and a piston 38 designed to perform a stroke sufficient for actuating a lever 40, fixed by a screw 42 on the rod 44 of piston 38. The introduction of the syringe into said passage 18 causes a movement of lever 28 around its own pivot 30 and then the actuating of said optical detector 32 which controls the servomechanism 36–38. This in turn moves the lever 40 which actuates a switching valve to position the injector-gas chromatographic unit in the required working conditions. In this particular case, as it can be seen from FIG. 6, said lever 40 directly acts on valve 46 which closes the injection channel 24 of injector 16, while opens valve said when the body 20 of syringe has been introduced into passage 18. When the syringe 20 is removed from passage 18, said lever 28 returns to its starting position due to gravity action and acts again on said optical detector 32 and then on said servomechanism 36–38, to set the valve on its starting condition, in this particular case in the condition of closing the passage 24.

The shown device also comprises safety means, formed by a pivot 48 protruding in said passage 18 in a suitable position, downstream the protrusion 26 of lever 28. Said pivot 48 is mounted on a slide 50 (FIG. 2) movable in an opening 52 of the device body under the action of a flat spring 54 which is locked by a screw 56 and tends to stress the pivot 48—slide 50 group to the position in which pivot 48 interferes with the passage of the syringe body 20 inside channel 18.

The rod 44 of piston 38 has a protrusion 58 designed to act on said flat spring 54 to move the latter and pivot 48 backwards inside the opening 52 as far as completely clear the passage 18 after actuation of servomechanism 36–38. In this way, said pivot 48 ensures that injection is not performed in case the detector 32—servomechanism 36–38 group is not operating. In this particular case, the position of pivot 48 is defined by the length of needle 22 in such a way that, when the syringe body 20 is stopped by pivot 48, the needle 22 arrives near the injector valve 46 without touching the same.

From what has been said, it is obvious that the servomechanism 36–38 can be used to control other operations of the injector or analytical means downstream same, in alternative or jointly to the actuation of valve 46. In particular, said servomechanism can control a secondary cooling system, an exhaust at the end of injection, a possible gas injection near the valve during injection, a switching from a condition of carrier gas feeding at constant pressure to a condition of carrier gas feeding at constant flow, a possible drawing of a splitting flow rate and other operations of the gas chromatographic unit which are switched on or off at the beginning or at the end for the sample injection. Moreover, the device can be used with an automatic injector.

In particular, the shown means to detect the presence or absence of the syringe body in the passage 18 can be substituted by a position sensor acting on the basis of principles different than those of the mentioned optical detector. Also the control means of switching valves can vary and can be constituted by known alternative means to the shown cylinder-piston system. All these modifications must obviously be considered as coming within the scope of the present invention.

We claim:

1. A device for coordinating the position of an injection syringe needle in a gas chromatographic apparatus with at least one other operation of the gas chromatographic apparatus downstream of said device, said device comprising a first channel for introducing the injection syringe, said channel being substantially aligned with the injection channel of a gas chromatographic injector; at least one means for detecting the presence of the injection syringe at least at one point in said channel, wherein said detecting means comprises a position sensor and a lever rotatable around a lever axis substantially perpendicular to the axis of said first channel, wherein said lever has an arm and a shaped appendix, wherein said shaped appendix protrudes into said channel when said lever is in its rest position, and wherein said appendix is positioned so that, when an injection syringe is introduced into said channel past said at least one point, the injection syringe contacts said appendix and causes rotation of said lever about said lever axis from said rest position so that said arm acts on said position sensor to indicate detection of the presence of the injection syringe in the first channel at said at least one point; and at least one servomechanical means actuatable in response to said detecting means for controlling said other operation depending on whether or not the injection syringe is detected in the channel by said at least one detecting means.

2. A device according to claim 1, wherein said at least one detecting means controls said other operation by means of a switching valve and wherein said switching valve controls at least one operation of the gas chromatographic injector.

3. A device according to claim 2, further comprising locking means positioned in said first channel downstream of said at least one point, said locking means being actuatable in response to said servomechanical means (a) to prohibit passage of said injector syringe past a preselected point when said servomechanical means is not actuating said switching valve and (b) to allow such passage when said servomechanical means is actuating said switching valve.

4. A device according to claim 3, wherein said servomechanical means actuates an injection valve controlling the opening and closing of the injection channel of a gas chromatographic injector, and wherein said locking means is positioned so that the tip of the needle of the injection syringe does not contact said injection valve when said locking means is in its locking position.

5. A device according to claim 1 or 3, wherein said position sensor is an optical sensor.

6. A device according to claim 1 or 3, wherein said servomechanical means comprises a fluidodynamically actuated cylinder-piston unit.

7. A device according to claim 6, wherein said cylinder piston unit is double-acting.

8. A device according to claim 6, wherein said cylinder piston unit is single-acting with automatic reversal, which piston is controlled by said detecting means.

9. A device according to claim 6, wherein said cylinder-piston unit mechanically controls the movements of at least one switching valve, as well as of a movable syringe retaining locking means.

* * * * *